United States Patent
Folger et al.

(10) Patent No.: US 9,993,485 B2
(45) Date of Patent: *Jun. 12, 2018

(54) HIGHLY CONCENTRATED STABLE MELOXICAM SOLUTIONS FOR NEEDLELESS INJECTION

(71) Applicant: Boehringer Ingelheim Vetmedica GmbH, Ingelheim am Rhein (DE)

(72) Inventors: Martin A. Folger, Ingelheim am Rhein (DE); Stefan Henke, Kirchen (DE); Bernhard Hassel, Ockenheim (DE); Bernd Zierenberg, Bingen am Rhein (DE)

(73) Assignee: Boehringer Ingelheim Vetmedica GmbH, Ingelheim am Rhein (DE)

(*) Notice: Subject to any disclaimer, the term of this patent is extended or adjusted under 35 U.S.C. 154(b) by 65 days.

This patent is subject to a terminal disclaimer.

(21) Appl. No.: 14/526,973

(22) Filed: Oct. 29, 2014

(65) Prior Publication Data

US 2015/0051198 A1 Feb. 19, 2015

Related U.S. Application Data

(63) Continuation of application No. 14/078,953, filed on Nov. 13, 2013, now Pat. No. 8,920,820, which is a continuation of application No. 11/845,675, filed on Aug. 27, 2007, now abandoned, which is a continuation of application No. 10/314,586, filed on Dec. 9, 2002, now abandoned.

(30) Foreign Application Priority Data

Dec. 12, 2001 (DE) .................. 101 61 077

(51) Int. Cl.
*A61K 31/5415* (2006.01)
*A61K 47/10* (2017.01)
*A61K 47/18* (2017.01)
*A61K 9/00* (2006.01)

(52) U.S. Cl.
CPC ........ *A61K 31/5415* (2013.01); *A61K 9/0021* (2013.01); *A61K 47/10* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 2,795,529 A | 6/1957 | Alburn et al. | |
| 3,089,818 A | 5/1963 | Stone et al. | |
| 3,288,675 A * | 11/1966 | Newmark | A61K 9/0019 514/157 |
| 4,482,554 A * | 11/1984 | Gebhardt | A61K 9/0019 514/226.5 |
| 4,628,053 A | 12/1986 | Fries | |
| 4,942,167 A | 7/1990 | Chiesi et al. | |
| 5,380,934 A | 1/1995 | Inoue et al. | |
| 6,053,890 A | 4/2000 | Moreau Defarges et al. | |
| 6,090,800 A | 7/2000 | Unger et al. | |
| 6,221,377 B1 * | 4/2001 | Meyer | A61K 33/00 424/434 |
| 7,105,512 B2 | 9/2006 | Morizono et al. | |
| 8,920,820 B2 * | 12/2014 | Folger | A61K 9/0021 424/400 |
| 2001/0055569 A1 | 12/2001 | Davis et al. | |
| 2002/0035107 A1 * | 3/2002 | Henke | A61K 9/0019 514/226.5 |
| 2002/0058908 A1 | 5/2002 | Zierenberg et al. | |
| 2002/0131998 A1 | 9/2002 | Martani | |
| 2003/0055051 A1 * | 3/2003 | Morizono | A61K 9/0048 514/226.5 |
| 2003/0235589 A1 | 12/2003 | Demopulos et al. | |
| 2006/0079516 A1 * | 4/2006 | Henke | A61K 9/0019 514/224.2 |
| 2014/0066440 A1 | 3/2014 | Folger et al. | |
| 2014/0113893 A1 | 4/2014 | Folger et al. | |
| 2017/0035885 A1 | 2/2017 | Henke et al. | |

FOREIGN PATENT DOCUMENTS

| | | | | |
|---|---|---|---|---|
| CN | 1187356 A | 7/1998 | | |
| JP | 11139971 A | 5/1999 | | |
| JP | 2001172183 A | 6/2001 | | |
| WO | 1999049867 A1 | 10/1999 | | |
| WO | 1999062516 A1 | 12/1999 | | |
| WO | 2001037838 A1 | 5/2001 | | |
| WO | WO 0137838 A1 * | 5/2001 | ........... A61K 9/0048 | |
| WO | 2001064268 A1 | 9/2001 | | |

OTHER PUBLICATIONS

Handbook of Pharmaceutical Excipients, Edetic Acid and Edetates, 1986, American Pharmaceutical Association and The pharmaceutical society of Great Britain, 108-110, 7 pages.*
Abstract in English of JP11139971, 1999.
International Search Report for PCT/EP2002/013983 dated Apr. 23, 2003.
Saha et al., "Effect of solubilizing excipients on permeation of poorly water-soluble compounds across Caco-2 cell monolayers". European Journal of Pharmaceutics and Biopharmaceutics, vol. 50, No. 3, 2000, pp. 403-411, Abstract accessed at http://cat.inist.fr/?aModele=afficheN&cpsidt=798854, accessed on Aug. 13, 2010, 3 pages.
Winfield, "Ophthalmic Products-Chelating agents". Pharmaceutical Practice, Churchill Livingstone, 2004, p. 268.
"Committee for Veterinary Medicinal Products Meloxicam Summary Report (1)". The European Agency for the Evaluation of Medicinal Products, Jun. 1997, pp. 1-7.

* cited by examiner

Primary Examiner — Gigi Huang
(74) Attorney, Agent, or Firm — Judy Jarecki-Black

(57) ABSTRACT

An aqueous cyclodextrin-free solution of meloxicam suitable is provided for administration by needleless injection, containing a pharmacologically acceptable meloxicam salt of an organic or inorganic base and one or more suitable excipients.

14 Claims, No Drawings

HIGHLY CONCENTRATED STABLE MELOXICAM SOLUTIONS FOR NEEDLELESS INJECTION

The present invention relates to highly concentrated stable meloxicam solutions for intracutaneous or subcutaneous needleless injection for treating respiratory diseases and inflammation in mammals.

BACKGROUND OF THE INVENTION

Meloxicam (4-hydroxy-2-methyl-N-(5-methyl-2-thiazolyl)-2H-1,2-benzothiazine-3-carboxamide-1,1-dioxide) is an active substance which belongs to the group of NSAIDs (non-steroidal-anti-inflammatory drugs). Meloxicam and the sodium and meglumine salt thereof (N-methyl-D-glucamine salt) are described in EP-A-0 002 482. EP-A-0 002 482 shows, inter alia, the example of a 0.2% injectable solution of meloxicam consisting of the meglumine salt of the active substance, sodium chloride and water.

EP-A-0 945 134 discloses the pH-dependent solubility characteristics of meloxicam and its salts, i.e. the sodium salt, the ammonium salt and the meglumine salt, in aqueous solution. According to this, meloxicam is an active substance which does not dissolve readily in water. The meloxicam salts, particularly the meglumine salt, exhibit improved solubility as the pH increases between 4 and 10, as shown in Table 1 of EP-0 945 134. However, up till now it has only been possible to produce stable, clear, aqueous solutions with a low concentration of meloxicam. In addition to the in situ formation of a meloxicam salt, e.g. meglumine salt, and the addition of solubilisers, these solutions were required to have a pH in the range of maximum possible solubility as well as being reasonably well tolerated and contain a high proportion of organic solvent. Attempts to produce formulations with the same or a similar recipe led to cloudiness of the solution, e.g. if the meloxicam concentrations were higher, e.g. 2%.

WO9959634 A1 describes an eye drop solution containing 0.5% meloxicam but makes no reference to possible meloxicam concentrations over 1%. A commercially available 0.5% meloxicam solution is used in small animals such as dogs, heifers and calves to treat respiratory diseases and inflammation, for example.

An active substance for needleless injection makes it possible for the animal keeper himself to administer a sterile solution to the animal. The requirements imposed on an active substance solution for needleless injection include inter alia small injectable volumes, the possibility of weight-related dosage and maximum possible flexibility in the number of actuation processes per treatment unit. Accordingly, injection volumes of 50 µl per actuation, for example, are technically feasible. For this purpose, as described in DE10010123 A1, a sterile solution may be transferred under aseptic conditions into a sterile cartridge which is then inserted in the metering system.

It has not hitherto been possible to treat large farm animals with a meloxicam solution that could be injected without a needle. The low concentration of active substance in the injectable solution did not allow an acceptable, well tolerated injection volume. The administration of meloxicam solutions by needlefree injection requires that the solution be free from particles, as solutions of this kind are subject to the same requirements as solutions for parenteral administration. In addition to intracutaneous and subcutaneous administration transcutaneous administration should also be taken into consideration, involving administering the substance directly into the blood vessels. This latter route is directly comparable with intravenous administration by injection through a syringe. The method of administration by needle-free injection has a relevant effect on bioavailability, which will be greater than with intracutaneous or subcutaneous administration, as transcutaneous absorption also takes place with needle-free injection. Organic solvents, solubilisers and water-soluble substances can only be used in certain concentrations for reasons of drug tolerance. The problem of the present invention is to produce particle-free highly concentrated meloxicam solutions which are stable over long periods, which are suitable for needleless injection.

DESCRIPTION OF THE INVENTION

Surprisingly, it has been found that highly concentrated meloxicam solutions with a content of active substance ranging from 35 to 100 mg/ml which contain, in addition to a meloxicam salt and certain excipients, another excipient selected from among citric acid, lecithin, gluconic acid, tartaric acid, phosphoric acid and EDTA or the salts thereof, may be produced so as to be particle-free and stable over long periods. The stability was achieved with an unexpectedly small amount of organic solubilisers. The formulation was found to be stable even when subjected to the process of final sterilisation.

This results in the solution to the problem according to the invention, as a formulation of a meloxicam solution which contains, in addition to a meloxicam salt, small concentrations of solubiliser, a preservative, a buffer substance for achieving the optimum pH range and another excipient.

The invention relates, as described in claim 1, to aqueous cyclodextrin-free solutions of meloxicam for needle-free intracutaneous or subcutaneous administration which contain a pharmacologically acceptable meloxicam salt of an organic or inorganic base in a highly concentrated solution with 35 to 100 mg/ml of meloxicam together with suitable excipients. Subclaims 2-14 describe advantageous further features of the invention.

The formulation according to the invention overcomes the problem arising from the prior art of providing a solution of the active substance meloxicam which is suitable for needleless injection, by permitting a high concentration of active substance in a particle-free solution which is stable over the long term, having the composition described hereinafter.

The formulation according to the invention may contain, as the meloxicam salt, the meglumine, sodium, potassium or ammonium salt, preferably the meloxicam meglumine salt.

The solubilisers used may be, for example polyethyleneglycols, polyoxyethylene-polyoxypropylene copolymers (e.g. poloxamer 188), glycofurol, arginine, lysine, castor oil, propyleneglycol, solketal, polysorbate, glycerol, sorbitol, mannitol, xylitol, polyvinylpyrrolidone, lecithin, cholesterol, 12-hydroxystearic acid-PEG660-ester, propyleneglycol monostearate, polyoxy-40-hydrogenated castor oil, polyoxyl-10-oleyl-ether, polyoxyl-20-cetostearylether and polyoxyl-40-stearate or a mixture of sorbitol, mannitol and xylitol, preferably polyethyleneglycols, polyoxyethylene-polyoxypropylene copolymers, glycofurol, polyvinylpyrrolidone, lecithin, cholesterol, 12-hydroxystearic acid-PEG66O-esters, propyleneglycol monostearate, polyoxy-40-hydrogenated castor oil, polyoxyl-10-oleyl-ether, polyoxyl-20-cetostearylether and polyoxyl-40-stearate. Particularly preferred are polyethyleneglycols, glycofurol and polyoxyethylene-polyoxypropylene-copolymers, but especially polyethyleneglycols (e.g. Macrogol 300) and polyoxyethylene-polyoxypropylene copolymers (e.g. Poloxamer 188). The preservatives used may be, for example, ethanol, benzoic acid and the sodium or potassium salts thereof, sorbic acid and the sodium or potassium salts thereof, chlorobutanol, benzyl alcohol, phenylethanol, methyl, ethyl, propyl or butyl-p-hydroxybenzoates, phenol, m-cresol, p-chloro-m-cresol or benzalkonium chloride. Particularly preferred are ethanol, benzoic acid and the sodium or potassium salts thereof, sorbic acid and the sodium or potassium salts thereof, chlorobutanol, benzylalcohol, phenylethanol and methyl, ethyl, propyl or butyl p-hydroxybenzoates, but preferably ethanol, benzoic acid and the sodium or potassium salts thereof, sorbic acid and the sodium or potassium salts thereof, but especially ethanol.

The buffer system used to achieve a pH of between 8 and 10 may be, for example, glycine, a mixture of glycine and HCl, a mixture of glycine and sodium hydroxide solution, and the sodium and potassium salts thereof, a mixture of potassium hydrogen phthalate and hydrochloric acid, a mixture of potassium hydrogen phthalate and sodium hydroxide solution or a mixture of glutamic acid and glutamate. Glycine, a mixture of glycine and HCl and a mixture of glycine/sodium hydroxide solution, especially glycine, are particularly preferred.

Other suitable excipients are citric acid, lecithin, gluconic acid, tartaric acid, phosphoric acid and EDTA or the alkali metal salts thereof, preferably tartaric acid and EDTA or the alkali metal salts thereof, particularly disodium EDTA.

One embodiment of the invention contains, in addition to the meglumine or sodium salt of the meloxicam, polyethyleneglycols, glycofurol and/or polyoxyethylene-polyoxypropylene copolymers, but particularly polyethyleneglycols (e.g. Macrogol 300) and/or polyoxyethylene-polyoxypropylene copolymers (e.g. Poloxamer 188) as solubiliser, ethanol, benzoic acid and the sodium or potassium salts thereof or sorbic acid and the sodium or potassium salts thereof, but particularly ethanol, as preservative, and glycine, a mixture of glycine/HCl or a mixture of glycine/sodium hydroxide solution, but preferably glycine, as buffer and disodium EDTA as an additional excipient.

The formulation according to the invention may contain meloxicam in a concentration of 35-100 mg/ml, preferably 40-80 mg/ml, preferably 45-70 mg/ml, particularly preferably 50-60 mg/ml, especially 55 mg/ml.

The meglumine concentration may be between 30 and 50 mg/ml, preferably 35-45 mg/ml, preferably 38-42 mg/ml, especially about 40 mg/ml. The possible sodium, potassium and ammonium concentrations are calculated accordingly.

The concentration of the solubilisers may be in the range from 20-200 mg/ml, preferably 30-150 mg/ml, preferably 40-130 mg/ml, more preferably 50-120 mg/ml, especially 70-100 mg/ml.

The concentration of the preservative ethanol may be in the range from 100-200 mg/ml, preferably 120-180 mg/ml, more preferably about 150 mg/ml.

The concentration of the preservatives benzoic acid and the sodium or potassium salts thereof, sorbic acid and the sodium or potassium salts thereof, chlorobutanol, benzyl alcohol, phenylethanol, phenol, m-cresol and p-chloro-m-cresol may be in the range from 0.5-50 mg/ml, preferably 1-10 mg/ml, more preferably 3-5 mg/ml.

The concentration of the preservatives benzalkonium chloride, phenylmercury nitrate and methyl-, ethyl-, propyl- or butyl-p-hydroxybenzoates may be in the range from 0.01-4 mg/ml, preferably 0.02-3 mg/ml, more preferably 0.1-0.5 mg/ml.

The concentration of the buffer substances may be between 4 and 138 mg/ml, preferably between 5 and 20 mg/ml, more preferably between 8 and 10 mg/ml.

The concentration of the other excipients mentioned above, i.e. EDTA, citric acid, lecithin, gluconic acid, tartaric acid and phosphoric acid or the salts thereof may be in the range from 0.2-3 mg/ml, preferably 0.3-2.5 mg/ml, preferably 0.5-2 mg/ml, most preferably 0.6-1.5 mg/ml, and in particular 0.7-1.0 mg/ml.

Meglumine and meloxicam may be used in a molar ratio of between 9:8 and 12:8, preferably in a molar ratio of 11:8, but especially in a molar ratio of 10:8.

In the formulation according to the invention, meloxicam and the other excipient, particularly disodium EDTA, may be present in a weight ratio of between 100:1 and 35:1, preferably between 80:1 and 40:1, preferably between 70:1 and 45:1, more preferably between 60:1 and 50:1, most preferably between 58:1 and 52:1, in particular about 55:1.

The formulation according to the invention may have a shelf-life after opening of 28 days or more.

The shelf-life of the solution in the sealed original packaging may be 1 month or more, in particular between 1 month and 24 months, but at least between 1 month and 18 months, preferably between 1 month and 12 months, more preferably between 1 month and 9 months, most preferably between 1 month and 6 months, particularly between 1 month and 3 months.

The formulation according to the invention should have a pH of between 8 and 10, preferably between 8.5 and 9, more preferably a pH between 8.7 and 8.9, particularly 8.8.

The formulation according to the invention is suitable for treating pain, inflammation, fever, acute mastitis, diarrhoea, lameness, oncological indications, problems with the locomotor apparatus, and respiratory complaints in animals, preferably acute mastitis, diarrhoea, lameness, problems with the locomotor apparatus and respiratory complaints, especially acute mastitis, diarrhoea, lameness, problems with the locomotor apparatus and respiratory complaints, most preferably respiratory complaints and oncological indications. The treatment may be given in conjunction with antibiotic therapy.

The formulation according to the invention is suitable for treating animals, preferably mammals, more particularly domestic pets, working animals or farm animals.

The formulation according to the invention is suitable for treating animals, preferably animals up to 500 kg, particularly domestic pets from 1 kg upwards, more preferably from 2 to 70 kg, most preferably 5 to 60 kg, or large animals up to 750 kg, preferably 50 kg to 500 kg, most preferably 100 to 400 kg.

The dosage of the formulation according to the invention should correspond to 0.1 to 1.0 mg of active substance per kg of bodyweight, preferably 0.4 to 0.8 mg/kg of bodyweight, more preferably 0.5 to 0.7 mg/kg of bodyweight, particularly preferably 0.6 mg/kg of bodyweight.

The formulation according to the invention may be prepared using the methods of preparing aqueous liquid formulations known from the literature. For example, the appropriate excipients may be added to a meloxicam salt solution.

Various commercial materials for aqueous liquid formulations which will allow sealing under inert gas and/or final sterilisation by autoclaving in the finished container may be used as a packaging material for the formulation according to the invention. Such materials include for example ampoules or glass vials, particularly glass vials, e.g. 50 ml or 100 ml glass vials of glass Type I (according to Pharm.

Eur/USP) in conjunction with rubber stoppers made of ethylenepropylenenorbornene terpolymer (EPDM) and aluminium caps. Vials made of plastics, particularly COO (Cyclic Olefin Copolymer), and other types of rubber stoppers are also suitable.

The meloxicam solutions according to the invention will now be illustrated by the following Example. Anyone skilled in the art will be aware that the Example serves only as an illustration and is not to be regarded as restrictive.

EXAMPLE

4% Meloxicam Solution
Ingredients:

|  | g/100 ml |
| --- | --- |
| Meloxicam | 4.0 |
| Meglumine | 2.8 |
| Macrogol 300*[1] | 15.0 |
| Poloxamer 188*[2] | 5.0 |
| Ethanol | 15.6 |
| Glycine | 0.5 |
| EDTA-Na | 0.1 |
| 1M HCl | q.s. ad pH 8.8 |
| 1M NaOH | q.s. ad pH 8.8 |
| Water for injections | ad 100 ml |

*[1]obtainable from Brenntag, Plochingen, Germany
*[2]obtainable from C.H. Erbsloeh, Krefeld, Germany For example, dogs may be treated by needle-free injection with a 4% meloxicam solution according to the invention in a metered volume of 50 μl per spray jet in a precise dosage related to body weight. A dog weighing 10 kg can be treated with a dose of 0.2 mg of meloxicam per kg of body weight with precisely one spray jet. Therapeutic accuracy is ensured in this case in steps of 10 kg.

Method of Preparation:

4 g of meloxicam are dissolved in 50 ml of an aqueous meglumine solution (1.4 g/50 ml) at 90° C. The other excipients are added one after another to the solution according to the recipe given above. The pH is then adjusted to 8.8 using 1 M hydrochloric acid and 1 M sodium hydroxide solution. Water is added to the solution until a volume of 100 ml is obtained.

What is claimed:

1. An aqueous particle free highly concentrated meloxicam solution suitable for administration by needleless injection, comprising:
   35 to 80 mg/ml meloxicam;
   meglumine in amount such that the meglumine and meloxicam are present in a molar ratio of between 9:8 and 12:8;
   disodium EDTA in an amount such that the weight ratio of meloxicam to disodium EDTA is between 100:1 and 35:1;
   a polyethylene glycol;
   a polyoxyethylene-polypropylene copolymer; and
   ethanol;
   wherein the solution has a pH of between 8.5 and 9.

2. An aqueous particle free highly concentrated meloxicam solution suitable for administration by needleless injection, comprising:
   40 to 80 mg/ml meloxicam;
   meglumine in amount such that the meglumine and meloxicam are present in a molar ratio of between 9:8 and 12:8;
   disodium EDTA in an amount such that the weight ratio of meloxicam to disodium EDTA is between 100:1 and 35:1;
   a polyethylene glycol;
   a polyoxyethylene-polypropylene copolymer; and
   ethanol;
   wherein the solution has a pH of between 8.5 and 9.

3. The aqueous solution according to claim 1, wherein the solution is free of cyclodextrin.

4. The aqueous solution according to claim 2, wherein the solution is free of cyclodextrin.

5. The aqueous solution according to claim 1, wherein the solution has a shelf-life after opening of 28 days or more.

6. The aqueous solution according to claim 2, wherein the solution has a shelf-life after opening of 28 days or more.

7. The aqueous solution according to claim 1, wherein the meglumine and meloxicam are present in a molar ratio of 10:8.

8. The aqueous solution according to claim 1 wherein the solution further comprises a preservative.

9. The aqueous solution according to claim 8, wherein the solution further comprises glycine.

10. The aqueous solution according to claim 9, wherein the solution further comprises sodium hydroxide and/or hydrochloric acid.

11. The aqueous solution according to claim 1, wherein the solution further comprises glycine.

12. The aqueous solution according to claim 11, wherein the solution further comprises sodium hydroxide and/or hydrochloric acid.

13. The aqueous solution according to claim 1, wherein the solution has a long term shelf-life of 24 months or more in its original packaging.

14. A sterile cartridge containing a solution according to claim 1.

* * * * *

UNITED STATES PATENT AND TRADEMARK OFFICE
CERTIFICATE OF CORRECTION

| | | |
|---|---|---|
| PATENT NO. | : 9,993,485 B2 | |
| APPLICATION NO. | : 14/526973 | |
| DATED | : June 12, 2018 | |
| INVENTOR(S) | : Martin A. Folger | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 78 days.

Signed and Sealed this
Sixth Day of December, 2022

Katherine Kelly Vidal
*Director of the United States Patent and Trademark Office*